United States Patent [19]
Morris et al.

[11] Patent Number: 5,159,929
[45] Date of Patent: Nov. 3, 1992

[54] INSULATED RF SHIELD

[76] Inventors: G. Ronald Morris, 48 S. Montgomery Ave., Bay Shore, N.Y. 11706; Charles E. McMillen, 185 Cypress Dr., Versailles, Ky. 40383

[21] Appl. No.: 538,398

[22] Filed: Jun. 14, 1990

[51] Int. Cl.$^5$ .............................................. A61B 5/055
[52] U.S. Cl. ................................ 128/653.2; 174/35 R; 128/633
[58] Field of Search ..................... 128/653 A, 653 SC; 324/318, 324; 174/35 MS, 35 R

[56] References Cited

U.S. PATENT DOCUMENTS

| | | |
|---|---|---|
| 4,516,074 | 5/1985 | Sugimoto . |
| 4,613,820 | 9/1986 | Edelstein et al. . |
| 4,638,253 | 1/1987 | Jaskolski et al. . |
| 4,642,569 | 2/1987 | Hayes et al. . |
| 4,727,328 | 2/1988 | Carper et al. . |
| 4,733,189 | 3/1988 | Punchard et al. . |
| 4,737,716 | 4/1988 | Roemer et al. . |
| 4,763,075 | 8/1988 | Weigert ............................... 324/318 |
| 4,793,356 | 12/1988 | Misic et al. . |
| 4,794,338 | 12/1988 | Roemer et al. . |
| 4,795,975 | 1/1989 | Cox .................... 174/35 MS |
| 4,801,489 | 1/1989 | Nakagawa .............. 174/35 MS |
| 4,808,957 | 2/1989 | Furukawa . |
| 4,871,883 | 10/1989 | Guiol .............................. 174/35 MS |
| 4,871,969 | 10/1989 | Roemer et al. . |
| 4,896,001 | 1/1990 | Pitts ................................ 174/35 MS |
| 4,910,090 | 3/1990 | Kuhlman ...................... 174/35 MS |

FOREIGN PATENT DOCUMENTS 0132785  11/1985  Fed. Rep. of Germany ...... 128/653

Primary Examiner—Lee S. Cohen
Assistant Examiner—Robert L. Nasser
Attorney, Agent, or Firm—Amster, Rothstein & Ebenstein

[57] ABSTRACT

A RF shield, for use adjacent a portion of a patient's body during a magnetic resonance examination by magnetic resonance examination apparatus, includes an electrically and thermally conductive layer having a pair of opposed surfaces, and a pair of electrically and thermally insulative layers. One of the insulative layers is disposed adjacent one of the opposed surfaces for positioning intermediate the conductive layer and the patient's body portion to insulate the patient's body from the conductive layer, and the other of the insulative layers is disposed adjacent the other of the opposed surfaces for positioning intermediate the conductive layer and the magnetic resonance examination apparatus to insulate the magnetic resonance apparatus from the conductive layer.

25 Claims, 2 Drawing Sheets

INSULATED RF SHIELD

BACKGROUND OF THE INVENTION

The present invention relates to the field of magnetic resonance ("MR") investigation of matter, and more particularly to a radio frequency (RF) shield for use therein.

The present invention finds particular application in conjunction with nuclear magnetic resonance (MR) imaging of the living body for medical diagnosis purposes and will be described with particular reference thereto. This description will emphasize the need to protect portions of the body of the patient from the radio frequency (RF) energy used in MR equipment and its effects and the need to protect the receiver coils used in the MR equipment from undesired signals. However, it is to be appreciated that the present invention has utility at present, and may in the future have further utility, in other applications using MR to investigate, locate or analyze animate or inanimate objects, such as MR spectroscopy, material analysis, explosive detection, well logging and the like.

During MR examination, it is often necessary to continuously monitor the patient, especially where the patient is sedated, aged, or infirmed. Where pulse oximetry is used for continuously monitoring the patient, three factors require consideration: safety of the patient, interference to the MR image, and interference to related equipment used proximally to the patient during the MR examination, such as a pulse oximeter. Patient safety problems relate to the possibility of RF burns at the points where the sensor attaches to the patient or where the electrical cables may touch the patient. The patient cable can act as an antenna to conduct RF energy from the MR apparatus to the patient, causing small, but possibly deep RF burns. Even where the pulse oximeter sensor is used in conjunction with a conventional uninsulated RF shield, a variety of arduous, time-consuming and burdensome precautions must be taken including the use of special cables, maintenance of the cables without loops or coils, periodic checking of the skin under the sensor for heating or reddening, and the like. MR images may also be degraded due to interference resulting from electronic signals induced in the patient cable by the oximeter or by external pick-up.

Similar considerations are obtained and similar precautions must be taken in connection with any of a variety of conductive articles or apparatus containing conductive articles, which may be employed proximally to the patient during MR examination—for example, for monitoring or obtaining measurements from the patient, for providing treatment to the patient, or the like. Treatments which may prove useful for patients undergoing MR examination and may also find need for an RF shield include the precise administration of contrast agents to enhance the diagnostic characteristics of lesions, drug delivery for pain management, chemotherapy and the like, administration of shock therapy simultaneous with or followed by patient evaluation using MR techniques, evaluation of organs for use as implants, treatment in association with the performance of sample biopsy and/or surgery. Measurements which may prove useful, in addition to the oxygen saturation and heart rate measurements obtained through pulse oximetry, include blood pressure, temperature, R-wave or EKG wave form, EEG or brain wave activity, respiration and carbon dioxide levels, analysis of drugs in the bloodstream, and numerous measurements of the patient and/or equipment associated with MR-guided sample biopsy and/or laser surgery. Accordingly, while the present invention will be described here primarily in connection with the use of a pulse oximeter sensor within the shield, the principles of the present invention are equally applicable when a different conductive article is employed as part of other monitoring or treatment apparatus or even where the conductive article is absent.

In MR imaging for medical diagnosis, many situations exist where it is desirable to provide local shielding for a patient undergoing an examination. In some cases it is desired to eliminate the excitation of nuclei and/or the detection of the signal in certain regions of the body. In this manner, specific artifacts and/or noise normally present in the magnetic resonance image may be reduced or eliminated completely. In other situations, it is desired to attach devices for monitoring or providing life support to the patient during the examination (e.g., a pulse oximeter). In this case, the shield must block RF signals emanating from the device, the leads of the device and/or device attachments in order to eliminate the detection of these signals by the receiver coils. It may also be required that the shield at the same time block RF signals generated by the MR imaging equipment which would otherwise interfere with the proper operation of the attached device.

In the past, shielding requirements described above have been attempted to be satisfied using aluminum foil as a conductive shield. In one instance signals from the patient's arms were eliminated from MR images using aluminum foil sheets wrapped around the arms. In another instance a monitoring device was successfully operated while patients were undergoing MR examinations using aluminum foil wrapped around a sensor attached to the patient's hand.

A conductor, such as aluminum foil, located in a RF environment provides electromagnetic shielding in part due to the existence of eddy currents which are established on the surface of the conductor. The magnitude and distribution of the currents induced on the conducting surface depend directly upon specific details of the existing RF environment as well as the geometry and material properties of the conducting surface. As the induced currents may lead to large voltages on the surfaces of the conductive shield relative to the patient or the surroundings, arc discharges may occur which can damage the patient or electronic equipment. RF induced currents may also lead to dangerous temperature elevations of the oximeter sensor, cables and/or conductive shield Indeed, there has been at least one reported incident of a severe finger burn caused by using a pulse oximeter for monitoring during MR imaging.

Thus, while aluminum foil is inexpensive and readily available, its use as a conductive shield in the MR environment can be unsafe for the patient, lead to damage of equipment, and produce misleading or unreliable results. Therefore, there remains a need in the field of MR examination for a safe, reliable and effective RF shield.

Accordingly, it is an object of the present invention to provide an RF shield for use on or around a sample undergoing MR examination which electrically blocks RF signals from the MR equipment in a safe, reliable, and effective manner.

Another object is to provide such a shield which electrically protects selected portions of the body of the patient from the RF energy used and its effects in a safe, reliable, and effective manner.

A further object is to provide an embodiment in which such a shield may incorporate at least a portion of an electrically conductive article, such as a sensor used for monitoring the functioning of a patient's body.

It is also an object of the present invention to provide such an embodiment in which the shield protects the conductive article from the RF energy and its effects.

It is another object to provide such an embodiment in which the shield blocks undesirable RF signals resulting from the presence of the conductive article in order to eliminate the detection of these signals by the MR examining apparatus.

It is yet another object to provide such a shield which thermally protects a selected portion of the body of the patient from the RF energy used and its effects in a safe, reliable, and effective manner.

It is a further object to provide such a shield which is of simple, rugged, and economical construction.

SUMMARY OF THE INVENTION

The present invention is a RF shield configured to provide safe and reliable shielding of signals transmitted to or from a selected portion of the patient or to or from sensors or attachments during a MR examination. Specifically, the inventive shield comprises a continuous conducting surface coupled with multiple insulating surfaces. The use of insulated surfaces ensures that the conducting surface of the shield will not come in electrical or thermal contact with the patient or with the MR instrument.

Broadly speaking, the insulated RF shield is configured to form a sleeve. The shielded sleeve, when placed over a portion of the patient's body, such as an arm, blocks the RF energy transmitted by the MR instrument and prevents excitation of nuclei within the shield. Nuclei which are not excited by the MR instrument do not contribute to the resonant signal and in this way are safely eliminated from the measurement.

In one specific embodiment of the present invention, an insulated RF shield is configured to form a mitt or boot. The shielded mitt or boot when suitably grounded and placed over a patient's hand or foot, respectively, blocks RF noise coming from a sensor used to measure the oxygen saturation of blood flowing through the patient's finger or toe—e.g., a pulse oximeter sensor. The shielded mitt or boot also blocks RF energy transmitted by the MR instrument and allows proper operation of the patient monitoring equipment.

The use of insulated RF shields may also decrease the noise detected by the MR instrument. For example, noncoherent noise signals from selected portions of the patient's body (e.g., the arm) which would otherwise be detected by the receiver coils of the MR instrument are safely blocked by use of the shield. Thus the signal-to-noise performance of the MR instrument can be improved.

More importantly, the use of insulated RF shields protects the portions of the patient's body about which they are disposed from the thermal and electrical effects of the RF energy generated by the MR equipment.

Finally, the use of insulated RF shields also permits proper operation of the sensor of any patient monitoring or treatment equipment incorporated into the shield and further protects the MR equipment from any RF signals generated by the monitoring or treatment equipment.

More particularly, it has now been found that the above and related objects of the present invention are obtained in an RF shield, for use adjacent a portion of a patient's body during a magnetic resonance examination by magnetic resonance examination apparatus, comprising an electrically conductive layer having a pair of opposed surfaces, and a pair of electrically insulative layers. One of the insulative layers is disposed adjacent one of the opposed surfaces for positioning intermediate the conductive layer and the patient's body portion to insulate the patient's body from the conductive layer, and the other of the insulative layers is disposed adjacent the other of the opposed surfaces for positioning intermediate the conductive layer and other material to insulate the other material from the conductive layer.

In a preferred embodiment, an electrically conductive article is disposed adjacent the other insulative layer, the electrically conductive article being, for example, a device for obtaining measurements from the patient, a device for providing treatment to the patient, or at least a portion of a monitor for monitoring a function of the patient's body—e.g. a pulse oximeter sensor.

Preferably the conductive layer is also thermally conductive and the insulative layer is also thermally insulative. The shield may additionally include means for electrically grounding the conductive layer, such as means for electrically connecting the conductive layer to a shielded case of the oximeter control and monitoring console and/or the RF shielded room and/or an independent ground system, as well as means for thermally connecting the conductive layer to a heat sink.

Typically, the shield has the configuration and dimensions of an extremity of the patient's body and is in the form of a mitt or boot. Where the electrically conductive article is a pulse oximeter sensor, the conductive layer and the one insulative layer define one or more apertures extending therethrough enabling illumination of a portion of a patient's body by the pulse oximeter sensor and the reception of illumination from the body portion by the pulse oximeter sensor. The pulse oximeter sensor is preferably disposed at least partially adjacent the other of the opposed surfaces, optimally intermediate the other of the opposed surfaces and the other of the insulative layers.

BRIEF DESCRIPTION OF THE DRAWING

The above brief description, as well as other objects and features of the present invention, will be more fully understood by reference to the following detailed description of the presently preferred, albeit illustrative, embodiments of the present invention when taken in conjunction with the accompanying drawing wherein.

DETAILED DESCRIPTION OF THE PREFERRED EMBODIMENTS

Figure 1:
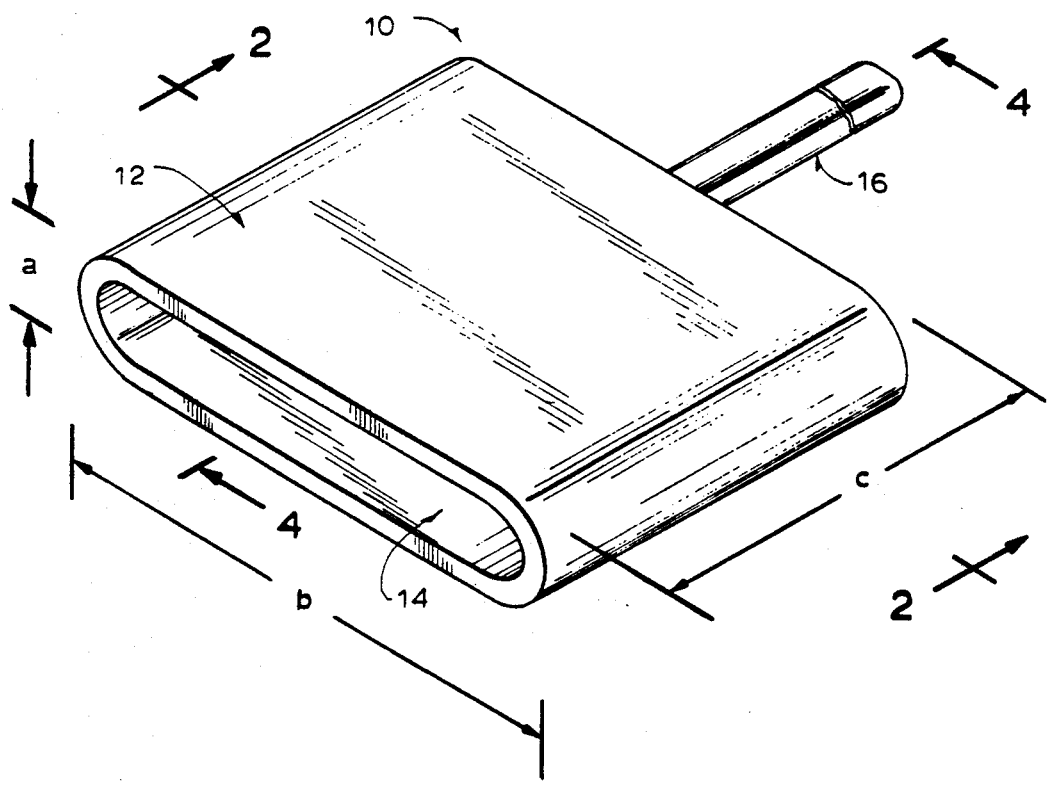
FIG. 1 is a fragmentary isometric view of a RF shield according to the present invention.
Figure 2:
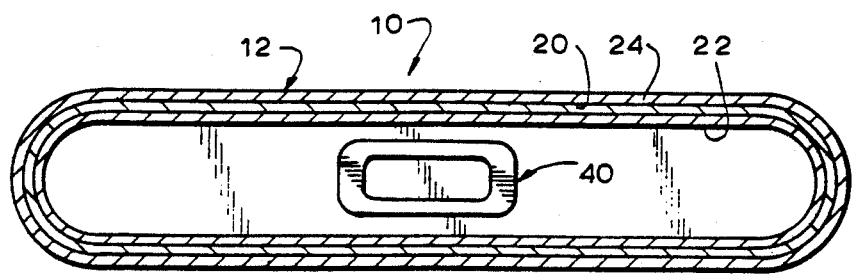
FIG. 2 is a sectional view thereof taken along the line 2—2 of FIG. 1.

Referring now to the drawing and in particular to FIGS. 1 and 2 thereof, therein illustrated is an insulated RF shield, generally designated by the reference numeral 10, according to the present invention. The shield 10 is configured as a mitt (or boot) having a hollow body portion 12 open at one end thereof to define an opening 14 for insertion of a human hand (or a human foot if the shield is configured as a boot) and the other end closed except for a shielded cable enclosure 16 for electrical connection to an oximeter sensor within the hollow body 12. The mitt 10 includes a continuous conducting layer 20, an inner continuous insulating surface 22 disposed on one surface of the conductive layer 20 and an outer insulative layer 24 disposed on the other surface of the conducting layer 20. The opening 14 of the body 12 has a height a of about 2 inches and a width b of about 4 inches, and the body 12 has a length c of about 8 inches.

Figure 3:
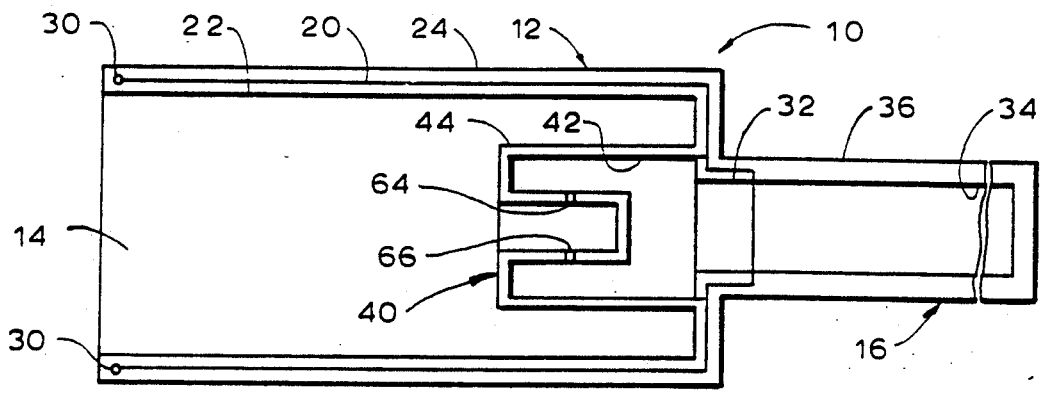
FIG. 3 is a fragmentary schematic side elevational view thereof.
Figure 4:
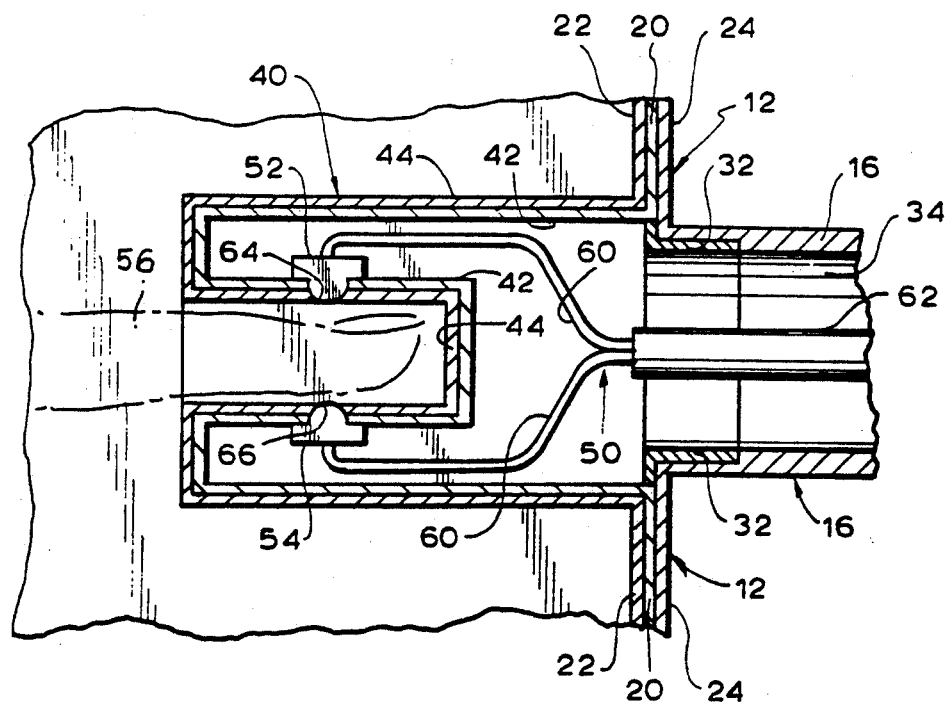
FIG. 4 is a sectional view thereof, to a greatly enlarged scale, taken along the line 4—4 of FIG. 1, and with a finger of a patient being illustrated in phantom line.

Referring now to FIGS. 3 and 4 for further details, the conductive layer 20 extends the full length of the body 12. Optionally, a conventional corona guard 30 is electrically attached to the entire exposed edge of the conductive layer 20 adjacent the opening 14. The opposite exposed edge of the conductive layer 20, adjacent the cable enclosure 16, is electrically secured to a bulkhead connector 32. Cable enclosure 16 includes a conductive cylinder 34 and an insulative cylinder 36 thereabout. The conductive cylinder 34 of cable enclosure 16 is also electrically connected to bulkhead connector 32, thereby establishing electrical connection between the conductive cylinder 34 of the cable enclosure 16 and the conductive layer 20 of the mitt body 12.

Disposed within the mitt body 12 is an insert generally designated 40. The insert 40 includes a conductive layer 42, which is electrically connected to the bulkhead connector 32, and an insulative layer 44. The insert 40 is configured and dimensioned to accept the finger of a patient (or to accept the toe of a patient in the case of a boot configuration), as well as the sensor of a monitoring device. It will be appreciated that the bulkhead connector 32 therefore establishes electrical connection between the conductive layers 20, 34, and 42 of the mitt body 12, cable enclosure 16 and insert 40, respectively. Similarly, the insulative layers 24 and 36 of the mitt body 12 and cable enclosure 16, respectively, are in insulative contact, as are the insulative layers 22 and 44 of the mitt body 12 and the insert 40, respectively. The insulative layers 22 and 24 of the mitt body 12 are in insulative contact as well (for example, about the corona guard 30), thereby putting all of the insulative layers 22, 24, 36, and 44 of the mitt body 12, cable enclosure 16, and insert 40 in continuous, uninterrupted insulative contact. Thus, the conductive layer 20 of the mitt body 12 and the conductive layer 42 of the insert 40 are effectively insulated by the various insulative layers 22, 24, 44 on either side thereof from both the MR apparatus and the patient.

Referring now to FIG. 4 in particular, the sensor, generally designated 50, of a pulse oximeter is disposed within the insert 40. The sensor 50, and indeed the entire pulse oximeter, may in turn be part of a device for providing treatment to a patient which includes a pulse oximeter of similar device for monitoring the patient during such treatment. The sensor 50 is of the conventional transmission type typically employed for use outside an MR instrument and consists of one or more light emitters 52 and one or more photodetectors 54. As illustrated, the light emitter 52 and photodetector 54 are disposed on opposite sides of the finger 56 illustrated in the phantom line in FIG. 4 (or a toe if the shield is in the configuration of a boot), with the photo- detector 54 detecting the light emitted by the emitter 52 and passing through the finger 56. It will be appreciated, however, that in an alternate embodiment the sensor is of the conventional reflectance type typically employed for use outside an MR instrument and consists of one or more light emitters and one or more photodetectors disposed on the same side of the finger (or toe), with the photodetectors detecting not the transmission of light through the finger but rather the reflection of light by the finger. Both of these types of pulse oximeter sensors are well known in the art and further explanation thereof is not deemed necessary herein.

Regardless of the type of pulse oximeter sensor used, electrical wires 60 from a wire harness 62 connect the light emitter 52 and photodetector 54 to the conventional control and display module (not shown) of the pulse oximeter. Electrical signals from that control module of the pulse oximeter activate the light emitter 52, causing light to shine on finger 56 through a small hole 64 in the insert 40. Light transmitted through the patient's finger 56 is detected by the photodetector 54 through the small hole 66 in the insert 40. The transmitted light contains encoded information which may be used to measure the heart rate and arterial hemoglobin oxygen saturation of the patient. The small openings 64, 66 in insert 40 do not basically interfere with the substantial protection afforded by the insulative layer 44 intermediate the conductive layer 42 of the insert and the patient's finger 56. If desired, the small openings 64, 66 may be filled with an appropriate light-transmitting composition, preferably an insulative light-transmitting composition (not shown). Likewise, the small openings 64, 66 in insert 40 do not basically interfere with the substantial shielding afforded by the conductive layer 42 of the insert. If desired, the small openings 64, 66 may be modified using conductive wire or mesh (not shown) attached to conductive layer 42 of the insert 40.

The insert 40 preferably has the configuration of an M with the two inner short legs defining a volume to receive the finger 56 (or toe where the shield is configured as a boot). The annulus between the inner short legs and the outer long legs of the M-shaped insert 40 receives the wires 60, with the light emitter 52 and photodetector 54 being disposed in alignment on opposite ones of the two inner short legs.

The area of opening 14 is preferably as small as practical while still allowing entry of the hand into the mitt body 12 (or entry of the foot into boot body 12). Effective shielding of sensor radiation and MR instrument interference requires in part that the solid angle subtended by the opening and the sensor be small. Thus, the length c of mitt body 12 is determined by the degree of shielding required and the area, determined by a and b, of opening 14.

An estimate of the maximum amount of shielding which might be expected can be obtained by considering a wave guide of rectangular dimensions. The cutoff frequency of a rectangular wave guide transmitting in the TE mode is calculated by equating the wave length at cutoff frequency to two times the larger cross sectional dimension. For frequencies below the cutoff frequency, the dB attenuation is equal to 54.5 times the length of the wave guide divided by the cutoff wave length. Thus a rectangular wave guide 2 inches high, 4 inches wide and 8 inches long would have a cutoff wave length of about 20 cm, corresponding to a cutoff frequency of more than 1400 MHz. This frequency is nearly an order of magnitude larger than the highest operating frequencies of present day whole body MR imaging systems. For frequencies less than the cutoff frequency the attentuation would be 54.5 dB, which corresponds to more than a 500 times amplitude reduction.

Conductive layer 42 is employed as an element of the insert 40 within the mitt 10 in part to eliminate eddy currents which would otherwise be established on the surface of the finger 56 as a consequence of the electronic signals in the wires 60 connecting the light emitter 52 and the photodectector 54. If eddy currents are allowed to be established on the surface of the patient (i.e., the skin), they can cause substantial undesirable noise in the receiver coils of the MR instrument. This is the case as the receiver coils are closely coupled to the body of the patient to allow detection of the very small signals stimulated by the MR instrument. In the prior art, aluminum foil was used as a shield to block radiation coming from the sensor, as a shield to block radio frequency energy transmitted by the MR instrument, and as a conductor to electrically short the eddy currents established on the surface of the patient.

The light emitter 52 and photodetector 54, along with the attached electrical wires 60 and wiring harness 62, are completely contained within the volume defined by conductive layers 34 and 42. Configuration of the shield 10 in this manner prohibits the establishment of eddy currents on the surface of the patient. In turn, it is no longer necessary to electrically short these eddy currents to keep them from being detected by the receiver coils of the MR instrument. Therefore, electrical insulative layers 22, 44 can be employed to safely insulate the patient from the electrically conductive layer 20, 42.

Further significant design considerations of mitt 10 are the thickness and electrical properties of conductive layers 20, 34, and 42. When the shielded mitt is located in a RF environment, eddy currents will be established on the surface of the conductors. The skin depth (i.e., the characteristic depth of penetration of the eddy currents) is directly proportional to the square root of the resistivity of the conductor and inversely proportional to the square root of the frequency. It is important to employ conductors with sufficient thickness to contain the eddy currents and which have low resistivity to minimize heating effects.

Copper is an excellent material choice for conducting surfaces as it is readily available, relatively inexpensive, easy to bond, and has a resistivity equal to 60 percent of that for aluminum. A copper conductor has a skin depth of approximately 0.002 inches at 1.7 MHz and 0.0002 inches at 170 MHz. Thus a copper conductive layer of at least 1 mil, and preferably a few mils, in thickness will work well for most applications. It is important to note that extremely thick conductors would have a negative effect on the fidelity of the time-varying gradient magnetic fields typically employed in MR imaging. Since the frequency response of these pulsed gradient waveforms is on the order of a few kilohertz, conductors of a few mils thickness will not significantly degrade the time-varying magnetic fields. Aluminum and like conductive material may also be employed.

It is important to realize that a shield employed as described may absorb significant amounts of RF energy. This energy must be dissipated to the environment without harm to the patient. Both the total surface area of the conductor and the total heat capacity of the conducting mass are important for the dissipation of this energy and the safety of the patient. Accordingly, the various conductive layers 20, 34, 42 and the electrically conductive bulkhead 32 of the mitt 10 are therefore not only electrically conductive (see electrically conductive lead 72 leading to an electrical ground 74 such as the conventional shielded console or RF shielded room fragmentarily indicated in FIG. 4), but preferably also thermally conductive (see thermally conductive lead 76 leading to a conventional thermal sink 78 fragmentarily indicated in FIG. 4). Similarly, the various insulative layers 20, 24, 36, 44 of the mitt 10 are not only electrically insulative, but preferably also thermally insulative. The thermally conductive layers are conventionally connected to a heat sink of sufficient dimensions and heat capacity, for example, the shielded case of the oximeter control and monitor console, the MR shielded room, or the like.

Several excellent material choices exist for insulative layers 22, 24, 36, and 44. Important considerations are the insulator dielectric and thermal properties as well as ease of manufacture and durability. It is especially important to restrict material choice to those that exhibit little or no static magnetic effects. With this restriction, magnetic field uniformity of high homogeneity is maintained.

RF noise signals caused by an oximeter sensor attached to a patient undergoing a MR examination are safely and effectively blocked from the receiving coils using the insulated shield disclosed above. In addition, RF energy transmitted by the MR instrument is blocked by the insulated shield, allowing proper operation of the monitoring device. The surface area and heat capacity of the insulated shield allow absorbed RF energy to be dissipated without harm to the patient. The unique configuration of the conducting surfaces employed allows the incorporation of an insulator. This in turn allows the patient to be safely isolated from the shield conductor, the monitoring equipment and/or the wall of the RF shielded room. In order to provide maximum shielding for the sensor 50 and sensor cable 60, mitt 10 can be terminated through shielded cable enclosure 16 at the RF shielded room and/or the shielded case of the oximeter control and monitor console and/or an independent ground system.

Obviously, the patient should be both electrically and thermally isolated to the greatest extent possible so that, even if he were to inadvertently be exposed to a live wire while himself being electrically grounded to the RF room, a potentially life-threatening condition would not develop.

It will be appreciated that insulated conductive shields can be configured for nearly all anatomical regions of the body—e.g., arm, leg, hand, foot, finger, toe, ear lobe, nose, etc. For example, for the human arm, the shield may be configured as a sleeve—that is, in the form of a hollow cylinder having an opening at either end. This sleeve is formed as a continuous conductive layer sandwiched between two continuous insulative layers, with appropriate corona guards being disposed along both exposed edges of the conductive layer. The area of the end openings are preferably as small as practical to allow entry of the arm. Effective shielding of nuclei from radiation transmitted by the MR instrument requires that the sleeve length be large compared to the diameter of the openings. Thus, the length of the sleeve is determined by the degree of shielding required and the area of the end openings.

An estimate of the amount of shielding which might be expected can be obtained by considering a wave guide of circular geometry. The cutoff wavelength for a circular wave guide transmitting in the TE mode is approximately 1.7 times the diameter of the cylinder and the attentuation far below cutoff is 32 dB per diameter of length. Thus, a 3 inch diameter sleeve 6 inches long would have a cutoff frequency of more than 2300 MHz and an estimated attenuation of 64 dB or more than 1500 times amplitude reduction.

The insulated conductive shields are preferably made of substantially flexible materials to facilitate the shields being placed on and removed from the patient's limb and to provide greater comfort to the patient wearing the same. It will be appreciated that, while the insulated conductive shields have been described in terms of mitts and boots for an entire hand or foot, respectively, the shield may consist of the insert 40 alone for a finger or toe, without any surrounding mitt or boot.

To summarize, the present invention provides an insulated RF shield for use on or around a sample undergoing MR examination which electrically blocks RF signals from the MR equipment and electrically protects selected portions of the body of the patient from the RF energy used and its effects, both in a safe, reliable and effective manner. Furthermore, the RF shield may incorporate at least a portion of an electrically conductive article, such as a sensor used for monitoring the functioning of a patient's body, and protect the conductive article from the RF energy and its effects while at the same time, blocking the detection by the MR examining apparatus of undesirable RF signals resulting from the presence of the conductive article. Additionally, the shield may be grounded to a shielded case of the oximeter control and monitor console and/or the RF shielded room and/or an independent ground system. The shield is of rugged and economical construction.

Now that the preferred embodiments of the present invention have been shown and described in detail, various modifications and improvements thereon will become readily apparent to those skilled in the art. Accordingly, the spirit and scope of the present invention is to be limited only by the appended claims, and not by the foregoing disclosure.

We claim:

1. A radio frequency shield for use adjacent an extremity of a patient's body during a magnetic resonance examination by magnetic resonance examination apparatus, comprising:
   (A) an electrically conductive layer having a pair of opposed surfaces;
   (B) a pair of electrically insulative layers, one of said insulative layers being disposed adjacent one of said opposed surfaces for positioning intermediate said conductive layer and the patient's extremity to insulate the patient's extremity from said conductive layer, and the other of said insulative layers being disposed adjacent the other side of said conductive layer and other material to insulate the other material from said conductive layer; and
   (C) an electrically conductive article disposed adjacent said other insulative layer;
   said conductive layer and said pair of insulative layers defining a shielding element essentially enclosing a volume including therein said electrically conductive article;
   said shield defining only a single aperture therethrough and being configured and dimensioned to receive therein through said aperture an extremity of the patient's body.

2. The shield of claim 1 wherein said electrically conductive article comprises means for obtaining measurements from the patient.

3. The shield of claim 1 wherein said electrically conductive article comprises means for providing treatment to the patient.

4. The shield of claim 1 wherein said electrically conductive article is at least a portion of a monitor for monitoring a function of the patient's body.

5. The shield of claim 2 wherein said electrically conductive article is at least a portion of a pulse oximeter sensor.

6. The shield of claim 1 additionally including means for electrically grounding said conductive layer.

7. The shield of claim 1 additionally including means for thermally sinking said conductive layer.

8. The shield of claim 1 additionally including means for electrically connecting said conductive layer to a shielded console.

9. The shield of claim 1 additionally including means for thermally connecting said conductive layer to a heat sink.

10. The shield of claim 1 wherein said shield has the configuration and dimensions of an extremity-receiving article selected from the group consisting of a mitt and a boot.

11. The shield of claim 1 wherein said shield is configured and dimensioned to receive therein an extremity of the patient's body, and said electrically conductive article is a pulse oximeter sensor.

12. The shield of claim 1 wherein said shield has the configuration and dimensions of an extremity-receiving article selected from the group consisting of a mitt and a boot, and said electrically conductive article is a pulse oximeter sensor.

13. The shield of claim 1 wherein said conductive layer has a thickness of at least 1 mil.

14. The shield of claim 1 wherein said conductive layer is also thermally conductive, and said insulative layer is also thermally insulative.

15. The shield of claim 1 additionally including means for electrically connecting said conductive layer to a RF shielded room.

16. A radio frequency shield for use adjacent a portion of a patient's body during a magnetic resonance examination by magnetic resonance examination apparatus, comprising:
   (A) an electrically conductive layer having a pair of opposed surfaces;
   (B) a pair of electrically insulative layers, one of said insulative layers being disposed adjacent one of said opposed surfaces for positioning intermediate said conductive layer and the patient's body portion to insulate the patient's body from said conductive layer, and the other of said insulative layers being disposed adjacent the other of said opposed surfaces for positioning intermediate said conductive layer and other material to insulate the other material from said conductive layer; and
   (C) an electrically conductive pulse oximeter sensor;

said conductive layer and said one insulative layer defining one or more apertures extending therethrough enabling illumination of a portion of a patient's body by said pulse oximeter sensor and the reception of illumination from the body portion by said pulse oximeter sensor.

17. The shield of claim 16 wherein said shield is configured and dimensioned to receive therein an extremity of the patient's body.

18. The shield of claim 16 wherein said pulse oximeter sensor is disposed at least in part adjacent said other of said opposed surfaces.

19. The shield of claim 18 wherein said pulse oximeter sensor is disposed at least in part intermediate said other of said opposed surfaces and said other of said insulative layers.

20. An radio frequency shield configured as a mitt or boot for use on a patient's extremity during a magnetic resonance examination by magnetic resonance examination apparatus, comprising a cover including:
   (A) an electrically and thermally conductive layer having a pair of opposed surfaces;
   (B) a pair of electrically and thermally insulative layers, one of said insulative layers being disposed on one of said opposed surfaces for positioning intermediate said conductive layer and the patient's body portion to insulate the patient's extremity from said conductive layer, and the other of said insulative layers being disposed on the other of said opposed surfaces for positioning intermediate said conductive layer and other material to insulate the other material from said conductive layer; and
   (C) an electrically conductive pulse oximeter sensor disposed at least partially intermediate said other of said insulative layer and said other of said opposed surfaces for monitoring a function of the patient's body;
   said conductive layer and said one insulative layer defining one or more apertures extending therethrough enabling illumination of a patient's extremity by said pulse oximeter sensor and the reception of illumination from the extremity by said pulse oximeter sensor.

21. The shield of claim 20 additionally including means for electrically grounding said conductive layer.

22. The shield of claim 20 additionally including means for thermally sinking said conductive layer.

23. The shield of claim 20 additionally including means for electrically connecting said conductive layer to a shielded console.

24. The shield of claim 20 additionally including means for electrically connecting said conductive layer to a RF shielded room.

25. The shield of claim 20 additionally including means for thermally connecting said conductive layer to a heat sink.

* * * * *